(12) United States Patent
Lim et al.

(10) Patent No.: US 11,421,237 B2
(45) Date of Patent: Aug. 23, 2022

(54) PAIR OF AMINO ACID SEQUENCES FOR MONITORING FORMATION OF TDP-43 OLIGOMER IN LIVING CELLS VIA BIMOLECULAR FLUORESCENCE COMPLEMENTATION

(71) Applicant: KOREA INSTITUTE OF SCIENCE AND TECHNOLOGY, Seoul (KR)

(72) Inventors: Sung Su Lim, Seoul (KR); Seul Gi Shin, Seoul (KR); Yun Kyung Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 197 days.

(21) Appl. No.: 16/857,089

(22) Filed: Apr. 23, 2020

(65) Prior Publication Data

US 2020/0340001 A1    Oct. 29, 2020

(30) Foreign Application Priority Data

Apr. 26, 2019 (KR) .................. 10-2019-0048923

(51) Int. Cl.
*C12N 15/64* (2006.01)
*C07K 14/47* (2006.01)

(52) U.S. Cl.
CPC .............. *C12N 15/64* (2013.01); *C07K 14/47* (2013.01)

(58) Field of Classification Search
None
See application file for complete search history.

(56) References Cited

FOREIGN PATENT DOCUMENTS

KR    1020150042308 A    4/2015
KR    1020180039471 A    4/2018

*Primary Examiner* — Anand U Desai
(74) *Attorney, Agent, or Firm* — Rabin & Berdo, P.C.

(57) ABSTRACT

The present disclosure relates to a vector pair for screening TDP-43 (TAR DNA-binding protein 43 or TransActive Response DNA-binding protein 43) oligomer formation, a cell line transfected with the vector pair, and a method of monitoring TDP-43 oligomer formation using the cell line. More specifically, the vector pair includes: a first vector including a first TDP-43 gene and a first fluorescence protein gene; and a second vector including a second TDP-43 gene and a second fluorescence protein gene, wherein a protein expressed from the first fluorescence protein gene and a protein expressed from the second fluorescence protein gene bind to each other to display fluorescence, by association between a protein expressed from the first TDP-43 gene and a protein expressed from the second TDP-43 gene. The vector pair is effective in that it makes it possible to monitor TDP-43 oligomer formation in living cells.

2 Claims, 3 Drawing Sheets
(2 of 3 Drawing Sheet(s) Filed in Color)
Specification includes a Sequence Listing.

PAIR OF AMINO ACID SEQUENCES FOR MONITORING FORMATION OF TDP-43 OLIGOMER IN LIVING CELLS VIA BIMOLECULAR FLUORESCENCE COMPLEMENTATION

BACKGROUND

Technical Field

The present disclosure relates to an amino acid sequence pair for monitoring interaction of TDP-43 in cells via bimolecular fluorescence complementation, a protein pair for screening TDP-43 oligomer formation, a nucleotide sequence pair encoding the same, a vector pair including the same, a cell line transfected with the vector pair, and a method of monitoring TDP-43 oligomer formation in living cells using the cell line.

Description of the Related Art

TDP-43 (TAR DNA-binding protein 43 or transactive response DNA-binding protein 43), a protein present mainly in the nucleus, inhibits gene transcription by binding to DNA or RNA, and is involved in gene expression by regulating RNA splicing and translation processes.

Initial studies have revealed that ubiquitinated TDP-43 protein is the major component of insoluble protein aggregates found in amyotrophic lateral sclerosis (ALS) and frontotemporal lobar degeneration (FTLD). Since then, cytoplasmic aggregates of TDP-43 protein have been found in various neurodegenerative brain diseases, including Alzheimer's disease (AD), Parkinson's disease (PD), dementia with lewy bodies (DLB), hippocampal sclerosis (HS), Alexander disease, Perry syndrome, argyrophilic grain disease (AG), corticobasal degeneration (CBD), progressive supranuclear palsy (PSP), and Huntington's disease (HD), and muscle degenerative diseases, including IBMPFD (inclusion body myopathy with Paget's disease of bone and/or frontotemporal dementia), sporadic inclusion body myositis (sporadic IBM), and myofibrillar myopathy. In addition, an abnormal increase of TDP-43 protein in the cytoplasm has been found in traumatic brain injury (TBI) animal models.

Accumulation of insoluble aggregates of this TDP-43 is a major symptom of various neurodegenerative diseases, but some studies conducted using TDP-43 expressing cell models or animal models have reported that TDP-43 overexpression alone without the formation of insoluble aggregates of TDP-43 also exhibits neurotoxicity. This led to the hypothesis that either the loss of normal function of TDP-43 by post-translational modifications (PTMs), such as phosphorylation, acetylation, fragmentation, ubiquitination, oxidation of cysteine residues, and SUMOylation, in intracellular stress cascades, or formation of toxic TDP-43 oligomers, causes neurodegeneration. Accordingly, studies on TDP-43 oligomers have been actively conducted.

However, conventional oligomer formation studies using TDP-43 recombinant protein have a problem in that PTMs cannot be regulated. In addition, they have a problem in that formation of the original oligomer cannot be accurately identified, since TDP-43 has a structural characteristic of spontaneously forming oligomers in vitro.

Therefore, there is an urgent need for a cell-based model that makes it possible to regulate the PTMs of TDP-43 in living cells, making it possible to observe the correct oligomer formation.

SUMMARY

The present disclosure has been made in order to solve the above-described problems, and an object of the present disclosure is to provide a reliable system for monitoring TDP-oligomer formation under the physiological conditions of living cells.

Another object of the present disclosure is to provide a cell model based on bimolecular fluorescence complementation (BiFC), which makes it possible to observe interaction between TDP-43 proteins in living cells.

However, the technical problems to be solved by the present disclosure are not limited to the above-mentioned problems, and other problems which are not mentioned will be clearly understood by those skilled in the art from the following description.

Hereinafter, various embodiments described herein will be described with reference to the accompanying drawings.

The present disclosure may undergo various modifications and have various embodiments, and thus specific embodiments are illustrated in the drawings and will be described in detail in the following detailed description. However, this description is not intended to limit the present disclosure to specific embodiments, and it should be understood that the present disclosure includes all modifications, equivalents or replacements that fall within the spirit and technical scope of the present disclosure. In the following description, when the detailed description of relevant known technology is determined to unnecessarily obscure the subject matter of the present disclosure, it may be omitted.

Terms used in the present specification are only to describe specific embodiments and are not intended to limit the scope of the present disclosure. Singular expressions include plural expressions unless otherwise specified in the context thereof. In the present specification, the terms "include", "comprise", "have", etc., are intended to denote the existence of mentioned characteristics, numbers, steps, operations, components, parts, or combinations thereof, but do not exclude the probability of existence or addition of one or more other characteristics, numbers, steps, operations, components, parts, or combinations thereof.

The terms "first", "second", etc., may be used to describe various components, but the components are not limited by the terms. The terms are used only for the purpose of distinguishing a component from other components.

Unless otherwise stated in the specification, all the scientific and technical terms used in the specification have the same meanings as commonly understood by those skilled in the technical field to which the present disclosure pertains.

A first aspect of the present disclosure is directed to a vector pair for screening TDP-43 oligomer formation, including: a first vector including a first TDP-43 (TAR DNA-binding protein 43 or TransActive Response DNA-binding protein 43) gene and a first fluorescence protein gene; and a second vector including a second TDP-43 gene and a second fluorescence protein gene, wherein a protein expressed from the first fluorescence protein gene and a protein expressed from the second fluorescence protein gene bind to each other to display fluorescence, by association between a protein expressed from the first TDP-43 gene and a protein expressed from the second TDP-43 gene.

Each of the first TDP-43 gene and the second TDP-43 gene may be a full-length TDP-43, a fragment of the full-length TDP-43, or a variant of the full-length TDP-43. For example, the TDP-43 gene may be a human full-length TDP-43 gene, a fragment thereof, or a variant having mutation in at least one nucleotide in the sequence of the human full-length TDP-43 gene. In addition, the TDP-43 gene may also be composed of the nucleotide sequence of SEQ ID NO: 1 or a fragment thereof. In one Example of the present disclosure, the TDP-43 gene set forth in SEQ ID NO: 1 was used.

It has been reported that ubiquitination of TDP-43, abnormal aggregation of TDP-43, and the like appear in various neurodegenerative brain diseases, muscle degenerative diseases, traumatic brain injury, etc. Thus, studies on TDP-43 oligomer formation have been actively conducted. Nevertheless, in the past, oligomer formation was studied using TDP-43 recombinant protein. However, these studies using TDP-43 recombinant protein have a problem in that PTMs cannot be regulated. In addition, these studies have a problem in that formation of the original oligomer cannot be accurately identified, since TDP-43 has a structural characteristic of spontaneously forming oligomers in vitro. For this reason, cellular models that can induce and monitor TDP-43 binding in living cells can be useful tools for studying TDP-43 pathology and developing methods to prevent and reverse the process. For this reason, cellular models that can induce and monitor binding between TDP-43 proteins in living cells can be useful tools for studying TDP-43 pathology and developing methods capable of preventing and reversing the process of the pathology.

The first fluorescence protein gene and/or the second fluorescence protein gene may be configured such that a protein expressed from the first fluorescence protein gene and a protein expressed from the second fluorescence protein gene bind to each other to display fluorescence, by association between a protein expressed from the first TDP-43 gene and the second TDP-43 gene. That is, when association between a protein expressed from the first TDP-43 gene and a protein expressed from the second TDP-43 gene occurs, a protein expressed from the first fluorescence protein gene and a protein expressed from the second fluorescence protein gene preferably bind to each other simultaneously with or subsequently to the association, thereby displaying fluorescence. For example, each of the fluorescence proteins may be a Venus protein or a fragment thereof, and the first fluorescence protein gene may be represented by the nucleotide sequence of SEQ ID NO: 2 or a fragment thereof, and the second fluorescence protein gene may be represented by the nucleotide sequence of SEQ ID NO: 3 or a fragment thereof. In addition, the first fluorescence protein gene may be VN173, and the second fluorescence protein gene may be VC155.

The present disclosure is an application of a method for visualizing protein-protein interactions, which is based on a bimolecular fluorescence complementation (BiFC) technique of forming a fluorescence protein complex from non-fluorescent constituents attached to the proteins of interest (Annu. Rev. Biophys. 37: 465-487). The BiFC technique based on the Venus protein, a kind of yellow fluorescence protein (YFP), is based on the principle according to which, when two different target proteins approach each other for interaction, fluorescence protein fragments linked to the target proteins also approach each other, and as a result, reconstruction between the fluorescence protein fragments occurs to display fluorescence. The use of this technique makes it possible to visually observe that an interaction between two target proteins occurred. Thus, this technique has the advantage of enabling protein-protein interactions to be visually observed in an optimal physical/chemical environment in which protein-protein interactions in cells or tissue may occur and be maintained. This technique makes it possible to determine not only a position where protein-protein interactions in cells or tissue occur, but also information about movement of these proteins.

The protein that is used in the present disclosure may be the Venus protein. The Venus protein can be effectively used for analysis of proteins such as TDP-43 protein, which are difficult to analyze spatially and temporally, because (1) it has fast and efficient maturation, (2) its self-assembly rate is low compared to that of other BiFC pairs, and (3) the fluorescence intensity of Venus-based BiFC is 10 times higher than that of EYFP-based BiFC (Biotechniques 40: 61-66; Biotechniques 49: 793-805).

According to one embodiment of the present disclosure, the first TDP-43 gene and the first fluorescence protein gene may be operably linked to each other, and the second TDP-43 and the second fluorescence protein gene may be operably linked to each other. Namely, in each of the first vector and the second vector, the TDP-43 gene and the fluorescence protein gene are preferably sequentially expressed by a single promoter. For example, the first TDP-43 gene and the first fluorescence protein gene may be linked to each other by a first linker, and the second TDP-43 gene and the second fluorescence protein gene may be linked to each other by a second linker. In an example of the present disclosure, the first linker represented by the nucleotide sequence of SEQ ID NO: 4 or a fragment thereof was used, and the second linker represented by the nucleotide sequence of SEQ ID NO: 5 or a fragment thereof was used.

The first vector and the second vector may each include a neuron-specific promoter. The first vector may include a first neuron-specific promoter, and the second vector may include a second neuron-specific promoter. The first neuron-specific promoter and/or the second neuron-specific promoter serves to express the vector pair of the present disclosure in neuron-related tissue, is not particularly limited, and may include any promoter known in the art. For example, the first neuron-specific promoter and/or the second neuron-specific promoter may be a CMV promoter and/or a Thy1 promoter, preferably CMV promoter. Since the Thy1 promoter is expressed specifically in neurons, it can induce expression of the genes inserted in the vector in neurons or neural tissue, particularly brain tissue.

The present disclosure is characterized in that, when the vector pair including the first vector and the second vector is expressed, a protein expressed from the first fluorescence protein gene and a protein expressed from the second fluorescence protein gene bind to each other to display fluorescence, by association between a protein expressed from the first TDP-43 gene and a protein expressed from the second TDP-43 gene. In particular, the present disclosure is characterized in that the genes inserted in the vector can be expressed by the neuron-specific promoter in neurons or neural tissue, particularly brain tissue. Accordingly, TDP-43 oligomer formation occurring in living cells can be visualized directly by fluorescence, thereby monitoring and quantifying the TDP-43 oligomerization process.

According to one embodiment of the present disclosure, in the case of the first vector, the first fluorescence protein gene may be linked to the N-terminus or C-terminus of the TDP-43 gene, and particularly, the first fluorescence protein gene is preferably linked to the C-terminus of the TDP-43 gene. In addition, in the case of the second vector according to the present disclosure, the second fluorescence protein gene may be linked to the N-terminus or C-terminus of the TDP-43 gene, and particularly, the second fluorescence protein gene is preferably linked to the C-terminus of the TDP-43 gene. This is believed to be because structurally positioning the TDP-43 gene ahead of the fluorescence protein gene in both the first and second vectors can further increase the luminous effect of the fluorescence proteins due to the interaction (or binding) of the TDP-43 proteins expressed from the genes.

According to one embodiment of the present disclosure, each of the first vector and second vector including the CMV promoter may be a pCMV6 including the CMV promoter, but is not limited thereto.

In addition, the TDP-43 gene and the first fluorescence protein gene may be inserted in the XhoI site of the pCMV6 vector, but may not be limited thereto. Furthermore, the TDP-43 gene, the second fluorescence protein gene and the second linker may be inserted in the XhoI site of the pCMV6 vector, but may not be limited thereto.

In addition, the first vector may include the nucleotide sequence of SEQ ID NO: 6, and the second vector may include the nucleotide sequence of SEQ ID NO: 7, but the scope of the present disclosure may not be limited thereto.

Moreover, the present disclosure may be directed to a vector pair for screening TDP-43 oligomer formation including: a first vector in which the TDP-43 gene represented by SEQ ID NO: 1, the first linker represented by SEQ ID NO: 4 and the first fluorescence protein gene represented by SEQ ID NO: 2 are operably linked to one another and which includes a CMV6 promoter; and a second vector in which the TDP-43 gene represented by SEQ ID NO: 1, the second linker represented by SEQ ID NO: 5 and the second fluorescence protein gene represented by SEQ ID NO: 3 are operably linked to one another and which includes a CMV6 promoter.

The second aspect of the present disclosure is directed to a recombinant vector including the above-described vector pair. The recombinant vector may be a single vector including the above-described vector pair, or may also be a pair of a first recombinant vector and a second recombinant vector, which include the first vector and the second vector, respectively.

A third aspect of the present disclosure is directed to a cell line transfected with the above-described recombinant vector. The cell line may be a cell line transiently transfected with the recombinant vector, or may be a cell line transfected with the recombinant vector for a long time or continuously.

As shown in the examples described below, the present inventors transfected HEK cells with the vector pair according to the present disclosure. Among these cells, cell lines having an excellent luminous effect were subcultured to obtain a stable cell line (KIST_HT43B1). The obtained cell line was deposited with the Korean Collection for Type Cultures, the Korea Research Institute of Bioscience and Biotechnology (KRIBB) under accession number KCTC13819BP. Thus, the cell line according to the present disclosure may be the cell line deposited under accession number KCTC13819BP. This cell line has a remarkably excellent effect of displaying fluorescence by binding between the first fluorescence protein and the second fluorescence protein when TDP-43 expressed from the first vector and TDP-43 expressed from the second vector form an oligomer.

A fourth aspect of the present disclosure is directed to a composition for monitoring TDP-43 oligomer formation, the composition including proteins expressed by the vector pair. In addition, the present disclosure may also be directed to a composition for detecting TDP-43 binding or for screening a TDP-43 binding inhibitor, the composition including proteins expressed by the vector pair.

A fifth aspect of the present disclosure is directed to a method of monitoring TDP-43 oligomer formation in cells, the method including the steps of: treating the above-described cell line with a TDP-43 oligomer formation inducer and culturing the treated cell line; and performing immunoblot analysis on the cell line. The TDP-43 oligomer formation inducer may be one or more selected from the group consisting of forskolin, scriptaid, thapsigargin and ionomycin.

When the TDP-43 cell model according to the present disclosure was treated with forskolin, scriptaid, thapsigargin and ionomycin, the BiFC fluorescence in the treated cells increased greatly (7 times or more) compared to that in an untreated group. In particular, treatment with scriptaid greatly increased the fluorescence not only in the nucleus but also in the cytoplasm.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION

The present disclosure may be better understood with the following examples. However, the following examples are for the purpose of illustrating the present disclosure and are not intended to limit the scope of the present disclosure as defined by the appended claims.

In the following examples, in order to visualize interaction between TDP-43 proteins at the oligomer level, a TDP-43-BiFC cell model was constructed. In order to visualize TDP-43 oligomer formation in living cells, BiFC (bimolecular fluorescence complementation) was attached to a human full-length TDP-43 and expressed in cells, and the cells were treated with various drugs to regulate PTMs of the protein, thereby developing a cell model that makes it possible to observe TDP-43 oligomer formation.

The cell model according to the present disclosure was constructed using a Venus protein-based BiFC method in which the N-terminal and C-terminal non-fluorescent fragments of the Venus protein were fused to TDP-43.

In the model according to the present disclosure as a fluorescence "turn-on" approach, no fluorescence is observed when TDP-43 proteins are present as monomers, but Venus fluorescence is observed when TDP-43 proteins are associated with each other. Thus, it is possible to TDP-43 oligomerization in living cells without staining with a foreign molecule.

Examples

1. Construction of TDP-43-BiFC Sensor

Figure 1:
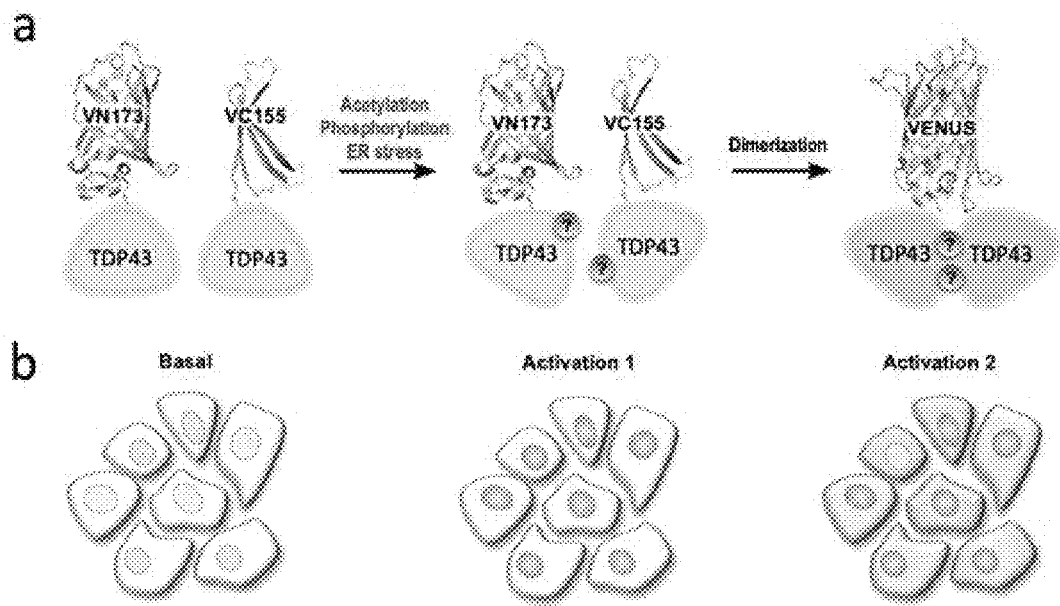
FIG. 1 is a schematic view showing the principle according to which TDP-43 fused to the Venus protein BiFC used in one example of the present disclosure acts as a Venus fluorescence turn-on sensor in cells in a normal state and a TDP-43 aggregation-induced state (FIG. 1a), and an increase in BiFC fluorescence and a change in the distribution of BiFC fluorescence (FIG. 1b).

FIG. 1a shows the principle according to which TDP-43 fused to the Venus protein BiFC acts as a Venus fluorescence turn-on sensor that shows TDP-43 interaction induced by PTM or intracellular stress. In a normal state, TDP-43 is present mainly in the nucleus, but when abnormal aggregation of TDP-43 is induced by various factors, including phosphorylation, fragmentation, acetylation, ubiquitination, cysteine residue oxidation, and SUMOylation, TDP-43 forms insoluble aggregates in the cytoplasm. FIG. 1b is a schematic view showing an increase in BiFC fluorescence and a change in the distribution of BiFC fluorescence in TDP-43-BiFC cells in a normal state and an aggregation-induced state.

Figure 2:
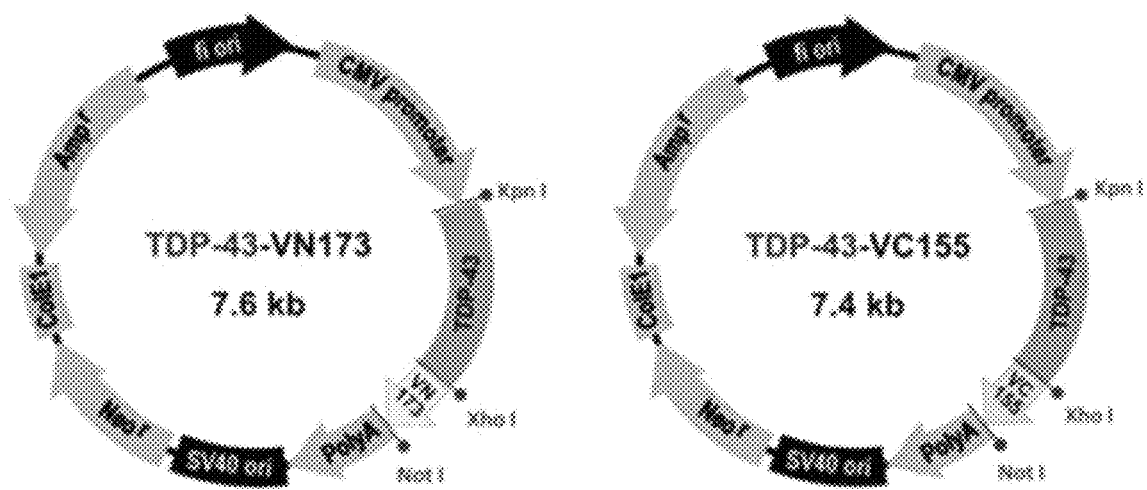
FIG. 2 is a vector map showing a structure in which two plasmids having BiFC labeled at the C-terminus of TDP-43, used in one example of the present disclosure, are inserted in a pCMV vector.

FIG. 2 is a vector map of a pCMV vector, which shows two plasmids having BiFC labeled at the C-terminus of TDP-43. In order to develop a TDP-43-BiFC cell line, the TDP-43-VN173 and TDP-43-VC155 constructs shown in FIG. 2 were co-transfected into HEK293 BiFC cells. For establishment of a stable cell line, the transfected cells were selected by culture with growth medium containing 100 µg/mL geneticin (G418; Sigma). In addition, the selected cells were sorted using FACSAria (BD Bioscience) into cells showing fluorescence. The sorted TDP-43-BiFC cells were kept in DMEM medium containing 10% FBS, 100 units/mL penicillin, 100 µg/mL streptomycin and 100 µg/mL G418 in a humidified atmosphere at 37° C. under 5% $CO_2$.

The nucleotide sequences of the TDP-43-BiFC genes inserted in the pCMV6 vector of FIG. 2, used for the transfection, are shown in Table 1 below.

TABLE 1

| | Nucleotide sequence |
|---|---|
| TDP43-VC173 (SEQ ID NO: 6) | ATG TCT GAA TAT ATT CGG GTA ACC GAA GAT GAG AAC GAT GAG CCC ATT GAA ATA CCA TCG GAA GAC GAT GGG ACG GTG CTG CTC TCC ACG GTT ACA GCC CAG TTT CCA GGG GCG TGT GGG CTT CGC TAC AGG AAT CCA GTG TCT CAG TGT ATG AGA GGT GTC CGG CTG GTA GAA GGA ATT CTG CAT GCC CCA GAT GCT GGC TGG GGA AAT CTG GTG TAT GTT GTC AAC TAT CCA AAA GAT AAC AAA AGA AAA ATG GAT GAG ACA GAT GCT TCA TCA GCA GTG AAA GTG AAA AGA GCA GTC CAG AAA ACA TCC GAT TTA ATA GTG TTG GGT CTC CCA TGG AAA ACA ACC GAA CAG GAC CTG AAA GAG TAT TTT AGT ACC TTT GGA GAA GTT CTT ATG GTG CAG GTC AAG AAA GAT CTT AAG ACT GGT CAT TCA AAG GGG TTT GGC TTT GTT CGT TTT ACG GAA TAT GAA ACA CAA GTG AAA GTA ATG TCA CAG CGA CAT ATG ATA GAT GGA CGA TGG TGT GAC TGC AAA CTT CCT AAT TCT AAG CAA AGC CAA GAT GAG CCT TTG AGA AGC AGA AAA GTG TTT GTG GGG CGC TGT ACA GAG GAC ATG ACT GAG GAT GAG CTG CGG GAG TTC TTC TCT CAG TAC GGG GAT GTG ATG GAT GTC TTC ATC CCC AAG CCA TTC AGG GCC TTT GCC TTT GTT ACA TTT GCA GAT GAT CAG ATT GCG CAG TCT CTT TGT GGA GAG GAC TTG ATC ATT AAA GGA ATC AGC GTT CAT ATA TCC AAT GCC GAA CCT AAG CAC AAT AGC AAT AGA CAG TTA GAA AGA AGT GGA AGA TTT GGT GGT AAT CCA GGT GGC TTT GGG AAT CAG GGT GGA TTT GGT AAT AGC AGA GGG GGT GGA GCT GGT TTG GGA AAC AAT CAA GGT AGT AAT ATG GGT GGT GGG ATG AAC TTT GGT GCG TTC AGC ATT AAT CCA GCC ATG ATG GCT GCC GCC CAG GCA GCA CTA CAG AGC AGT TGG GGT ATG ATG GGC ATG TTA GCC AGC CAG CAG AAC CAG TCA GGC CCA TCG GGT AAT AAC CAA AAC CAA GGC AAC ATG CAG AGG GAG CCA AAC CAG GCC TTC GGT TCT GGA AAT AAC TCT TAT AGT GGC TCT AAT TCT GGT GCA GCA ATT GGT TGG GGA TCA GCA TCC AAT GCA GGG TCG GGC AGT GGT TTT AAT GGA GGC TTT GGC TCA AGC ATG GAT TCT AAG TCT TCT GGC TGG GGA ATG ACG CGT ACG CGG CCG CTC GAG TCT AGA AGA TCC ATC GCC ACC ATG GTG AGC AAG GGC GAG GAG CTG TTC ACC GGG GTG GTG CCC ATC CTG GTC GAG CTG GAC GGC GAC GTA AAC GGC CAC AAG TTC AGC GTG TCC GGC GAG GGC GAG GGC GAT GCC ACC TAC GGC AAG CTG ACC CTG AAG CTG ATC TGC ACC ACC GGC AAG CTG CCC GTG CCC TGG CCC ACC CTC GTG AEC AEC CTG GGC TAC GGC CTG CAG TGC TTC GCC CGC TAC CCC GAC CAC ATG AAG CAG CAC GAC TTC TTC AAG TCC GCC ATG CCC GAA GGC TAC GTC CAG GAG CGC AEC ATC TTC TTC AAG GAC GAC GGC AAC TAC AAG AEC CGC GCC GAG GTG AAG TTC GAG GGC GAC AEC CTG GTG AAC CGC ATC GAG CTG AAG GGC ATC GAC TTC AAG GAG GAC GGC AAC ATC CTG GGG CAC AAG CTG GAG TAC AAC TAC AAC AGC CAC AAC GTC TAT ATC AEC GCC GAC AAG CAG AAG AAC GGC ATC AAG GCC AAC TTC AAG ATC CGC CAC AAC ATC GAG TAG |

TABLE 2

| | Nucleotide sequence |
|---|---|
| TDP43-VC155 (SEQ ID NO: 7) | ATG TCT GAA TAT ATT CGG GTA ACC GAA GAT GAG AAC GAT GAG CCC ATT GAA ATA CCA TCG GAA GAC GAT GGG ACG GTG CTG CTC TCC ACG GTT ACA GCC CAG TTT CCA GGG GCG TGT GGG CTT CGC TAC AGG AAT CCA GTG TCT CAG TGT ATG AGA GGT GTC CGG CTG GTA GAA GGA ATT CTG CAT GCC CCA GAT GCT GGC TGG GGA AAT CTG GTG TAT GTT GTC AAC TAT CCA AAA GAT AAC AAA AGA AAA ATG GAT GAG ACA GAT GCT TCA TCA GCA GTG AAA GTG AAA AGA GCA GTC CAG AAA ACA TCC GAT TTA ATA GTG TTG GGT CTC CCA TGG AAA ACA ACC GAA CAG GAC CTG AAA GAG TAT TTT AGT ACC TTT GGA GAA GTT CTT ATG GTG CAG GTC AAG AAA GAT CTT AAG ACT GGT CAT TCA AAG GGG TTT GGC TTT GTT CGT TTT ACG GAA TAT GAA ACA CAA GTG AAA GTA ATG TCA CAG CGA CAT ATG ATA GAT GGA CGA TGG TGT GAC TGC AAA CTT CCT AAT TCT AAG CAA AGC CAA GAT GAG CCT TTG AGA AGC AGA AAA GTG TTT GTG GGG CGC TGT ACA GAG GAC ATG ACT GAG GAT GAG CTG CGG GAG TTC TTC TCT CAG TAC GGG GAT GTG ATG GAT GTC TTC ATC CCC AAG CCA TTC AGG GCC TTT GCC TTT GTT ACA TTT GCA GAT GAT CAG ATT GCG CAG TCT CTT TGT GGA GAG GAC TTG ATC ATT AAA GGA ATC AGC GTT CAT ATA TCC AAT GCC GAA CCT AAG CAC AAT AGC AAT AGA CAG TTA GAA AGA AGT GGA AGA TTT GGT GGT AAT CCA GGT GGC TTT GGG AAT CAG GGT GGA TTT GGT AAT AGC AGA GGG GGT GGA GCT GGT TTG GGA AAC AAT CAA GGT AGT AAT ATG GGT GGT GGG ATG AAC TTT GGT GCG TTC AGC ATT AAT CCA GCC ATG ATG GCT GCC GCC CAG GCA GCA CTA CAG AGC AGT TGG GGT ATG ATG GGC ATG TTA GCC AGC CAG CAG AAC CAG TCA GGC CCA TCG GGT AAT AAC CAA AAC CAA GGC AAC ATG CAG AGG GAG CCA AAC CAG GCC TTC GGT TCT GGA AAT AAC TCT TAT AGT GGC TCT AAT TCT GGT GCA GCA ATT GGT TGG GGA TCA GCA TCC AAT GCA GGG TCG GGC AGT GGT TTT AAT GGA GGC TTT GGC TCA AGC ATG GAT TCT AAG TCT TCT GGC TGG GGA ATG <u>ACG CGT ACG CGG CCG CTC GAG AAG</u> CAG AAG AAC GGC ATC AAG GCC AAC TTC AAG ATC CGC CAC AAC ATC GAG GAC GGC GGC GTG CAG CTC GCC GAC CAC TAC CAG CAG AAC AEC CCC ATC GGC GAC GGC CCC GTG CTG CTG CCC GAC AAC CAC TAC CTG AGC TAC CAG TCC AAA CTG AGC AAA GAC CCC AAC GAG AAG CGC GAT CAC ATG GTC CTG CTG GAG TTC GTG AEC GCC GCC GGG ATC ACT CTC GGC ATG GAC GAG CTG TAC AAG TAA |

2. Induction of TDP-43 Oligomer Formation

The TDP-43-BiFC cells prepared in Example 1 above were treated with a compound that induces PTMs of protein, a compound that ER stress in cells, amyloid protein, metal ions, or the like, and changes in BiFC fluorescence in the cells were examined. Specifically, for fluorescence analysis, the TDP-43-BiFC cells were grown in a 384-well plate and treated with each of forskolin (30 μM), scriptaid (3 μM), thapsigargin (1 μM), ionomycin (1 μM), MG132 (5 μM), α-synuclein (5 μg/ml), tauK18$^{P301L}$ (5 μg/ml), Cu$^{2+}$ (1 μM) and Zn$^{2+}$ (30 μM), followed by culture at 37° C. for 48 hours. Fluorescence images were obtained using Operetta® (PerkinElmer), and the fluorescence intensity in the nucleus and the cytoplasmic fluorescence intensity were analyzed using Harmony3.1 software (PerkinElmer).

Figure 3:
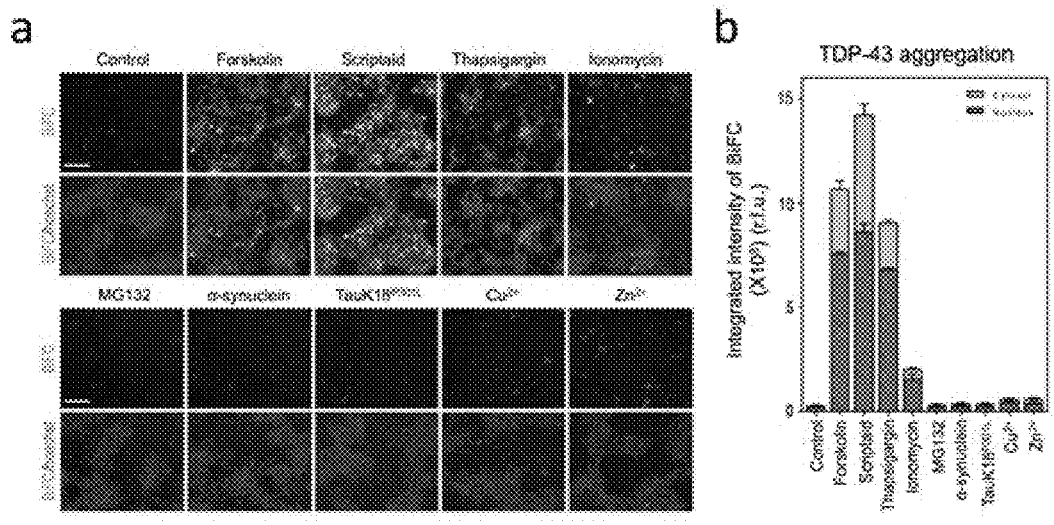
FIG. 3 shows the results of observing changes in BiFC fluorescence after treating TDP-43-BiFC cells with a compound that induces PTMs of protein, a compound that ER stress in cells, amyloid protein, metal ions, or the like, according to one example of the present disclosure.

FIG. 3 shows the results of observing changes in BiFC fluorescence after treating TDP-43-BiFC cells with a compound that induces PTMs of protein, a compound that ER stress in cells, amyloid protein, metal ions, or the like. As shown in FIG. 3, when the cells were treated with each of the compound scriptaid that induces phosphorylation, scriptaid that increases acetylation, thapsigargin, and ionomycin, the BiFC fluorescence in the cells increased 36-fold, 48-fold, 31-fold and 7-fold, respectively, compared to that in the untreated cells. However, when the cells were treated with proteasome inhibitor MG132, no change in the fluorescence was observed. When the cells were treated with each of α-synuclein and tauK18$^{P301L}$, which are amyloid proteins, the BiFC fluorescence of TDP-43 did not increase. When the cells were treated with each of Cu$^{2+}$ and Zn$^{2+}$, the BiFC fluorescence increased about 2-fold. From these results, it can be seen that the phosphorylation or acetylation of TDP-43 strongly induces TDP-43 oligomer formation, and even when intracellular ER stress is induced, TDP-43 oligomer formation greatly increases.

3. Change in Intracellular Distribution by TDP-43 Oligomer Formation.

Next, the pattern of intracellular distribution by an increase in TDP-43 oligomer formation was examined. Specifically, TDP-43 formation was induced in the same manner as Example 2 above, and then the whole plate was automatically imaged using Operetta®, and high-resolution images were obtained using a Nikon Eclipse inverted microscope (Ti, Nikon) at 1000× magnification.

Figure 4:
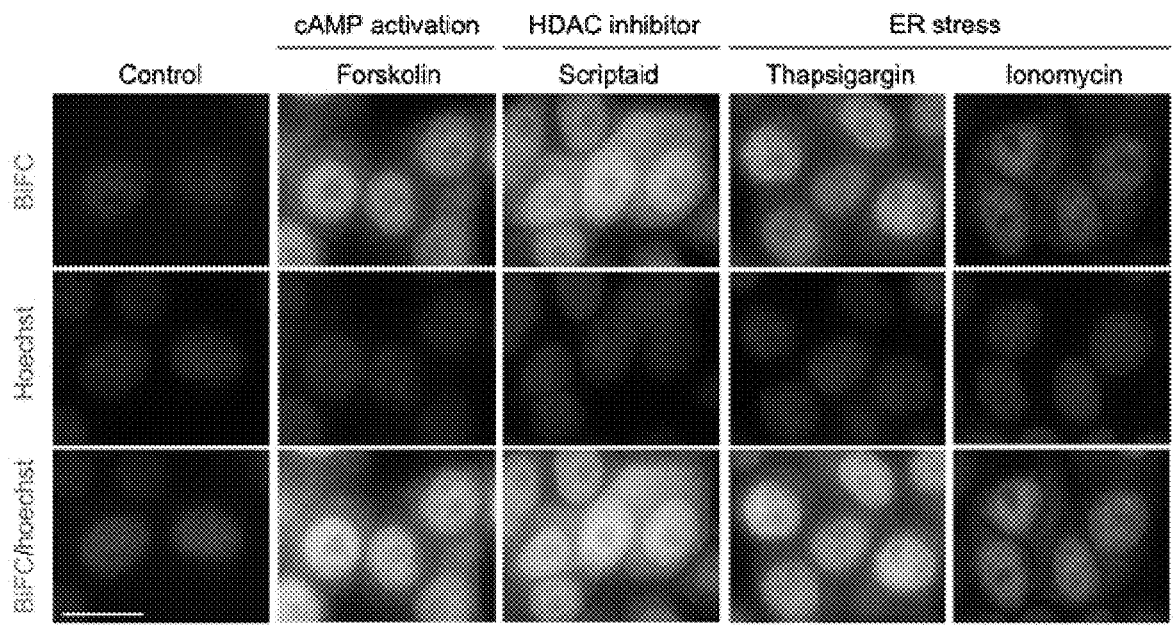
FIG. 4 shows high-magnification images obtained after treating TDP-43-BiFC cells with each of forskolin, scriptaid, thapsigargin and ionomycin according to one example of the present disclosure.

FIG. 4 shows high-magnification images obtained after treating the TDP-43-BiFC cells with each of forskolin, scriptaid, thapsigargin and ionomycin as described above. It can be seen that when the cells were treated with scriptaid, the BiFC fluorescence intensity in the cytoplasm increased. In addition, the control showed the BiFC fluorescence in the nucleus portion and showed very weak or almost no fluorescence in other portions, but when the cells were treated with scriptaid, the BiFC fluorescence significantly increased not only in the nucleus but also in the cytoplasm.

4. Isolation and Detection of TDP-43 Oligomer

Lysates of the TDP-43-BiFC cells treated with each of the four drugs in Example 3 and a lysate of untreated cells were prepared and TDP-43 oligomers were isolated therefrom. Specifically, TDP-43-BiFC cells were grown in a 6-well plate, treated with each of forskolin (30 μM), scriptaid (1

μM), thapsigargin (0.5 μM) and ionomycin (1 μM), and cultured at 37° C. for 24 hours, and then lysates of the cells were prepared. GFP-trap beads shown in FIG. 5a were added to the lysates which were then incubated at 4° C. for 16 hours, and the oligomerized TDP-43 protein was isolated. The isolated protein was separated by SDS-PAGE, and immunoblot analysis was performed using anti-TDP-43 antibody.

Figure 5:
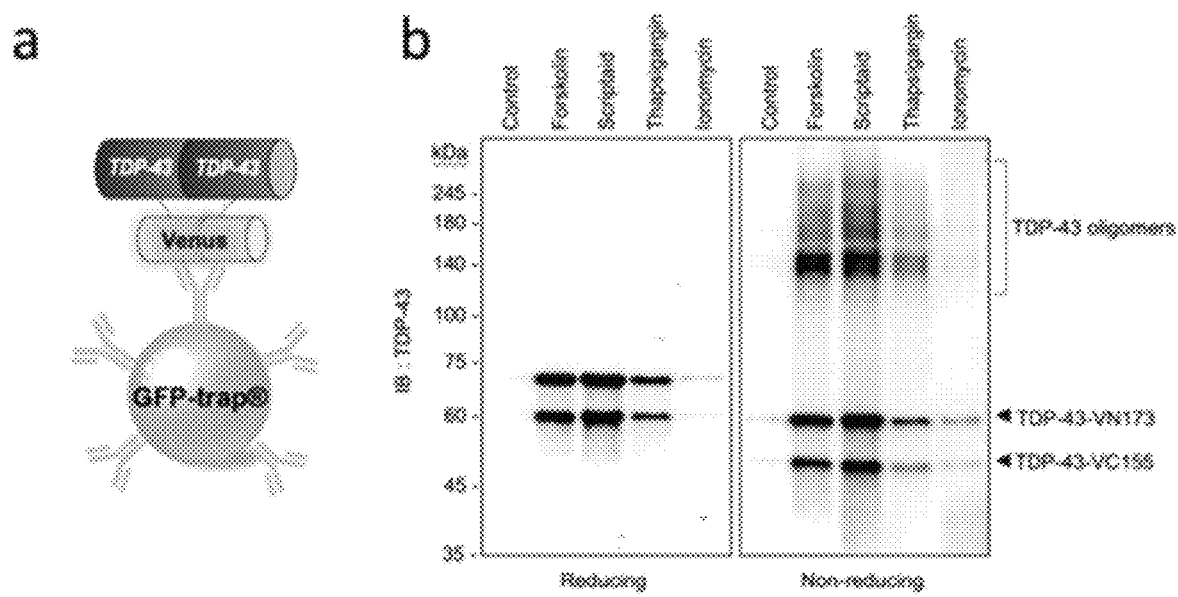
FIG. 5 shows the results of immunoblot analysis performed according to one example of the present disclosure by preparing lysates of TDP-43-BiFC cells treated with each of four drugs (forskolin, scriptaid, thapsigargin, and ionomycin) and a lysate of untreated cells and isolating TDP-43 oligomers from the lysates.

As can be expected from the results of measuring the BiFC fluorescence intensity in Example 2 (FIG. 3), when the cells were treated with each of the drugs, the amount of the detected oligomerized protein significantly increased compared to that in the untreated cells, and the largest amount of the oligomerized protein was detected in the cells treated with scriptaid, which showed the greatest increase in the BiFC fluorescence among the drugs. For the remaining drugs, the amount of the oligomer appeared in the same pattern as the change in the BiFC fluorescence intensity (left of FIG. 5b). From these results, it was confirmed that the degree of the BiFC fluorescence shown in the TDP-43-BiFC cells represents the amount of the TDP-43 oligomer. As can be seen in FIG. 5 showing the results of the immunoblot analysis in which disulfide bonds were not reduced, oligomers having a size of 100 kDa or more were detected together with monomers. These results suggest that the TDP-43 oligomers include oligomers formed through disulfide bonds together with oligomers formed without disulfide bonds.

As described above, according to the present disclosure, TDP-43 oligomer formation in living cells may be observed using a cell model based on bimolecular fluorescence complementation (BiFC).

In addition, according to the present disclosure, non-fluorescent constituents attached to TDP-43 display fluorescence when the physical distance therebetween becomes closer due to association between TDP-43 proteins, thus making it possible to observe interaction between two TDP-43 proteins.

According to the present disclosure, TDP-43 oligomer formation in living cells may be directly visualized, and thus the process of TDP-43 oligomer formation may be monitored and quantified. Therefore, the cell model according to the present disclosure may be used as a useful tool for studying the development of diseases related to TDP-43 and developing a method for preventing and reversing TDP-43 oligomer formation.

The scope of the present disclosure is defined not by the detailed description, but by the appended claims, and all variations and modifications derived from the meaning and scope of the claims and their equivalents are to be construed as being included in the scope of the present disclosure.

What is claimed is:

1. A vector pair for screening TDP-43 oligomer formation, comprising:
   a first vector comprising
      a first TDP-43 (TAR DNA-binding protein 43 or Trans-Active Response DNA-binding protein 43) gene composed of the nucleotide sequence of SEQ ID NO: 1, and
      a first fluorescence protein gene composed of the nucleotide sequence of SEQ ID NO: 2,
      wherein the first fluorescence protein gene is linked to C-terminus of the first TDP-43 gene; and
   a second vector comprising
      a second TDP-43 gene composed of the nucleotide sequence of SEQ ID NO: 1, and
      a second fluorescence protein gene composed of the nucleotide sequence of SEQ ID NO: 3,
   wherein the second fluorescence protein gene is linked to C-terminus of the second TDP-43 gene,
   wherein the first TDP-43 gene and the first fluorescence protein gene are linked to each other by a first linker composed of the nucleotide sequence of SEQ ID NO: 4, and the second TDP-43 gene and the second fluorescence protein gene are linked to each other by a second linker composed of the nucleotide sequence of SEQ ID NO: 5,
   wherein the first vector is composed of the nucleotide sequence of SEQ ID NO: 6, and the second vector is composed of the nucleotide sequence of SEQ ID NO: 7,
   wherein a protein expressed from the first fluorescence protein gene and a protein expressed from the second fluorescence protein gene bind to each other to display fluorescence, by association between a protein expressed from the first TDP-43 gene and a protein expressed from the second TDP-43 gene,
wherein the first TDP-43 gene and the first fluorescence protein gene are operably linked to each other, and the second TDP-43 gene and the second fluorescence protein gene are operably linked to each other.

2. A recombinant vector comprising the vector pair of claim 1.

* * * * *

SEQUENCE LISTING

```
<160> NUMBER OF SEQ ID NOS: 7

<210> SEQ ID NO 1
<211> LENGTH: 1242
<212> TYPE: DNA
<213> ORGANISM: Homo sapiens
<220> FEATURE:
<221> NAME/KEY: gene
<222> LOCATION: (1)..(1242)
<223> OTHER INFORMATION: TDP-43(TAR DNA-binding protein 43, transactive
      response DNA binding protein 43)

<400> SEQUENCE: 1
atgtctgaat atattcgggt aaccgaagat gagaacgatg agcccattga aataccatcg        60
gaagacgatg ggacggtgct gctctccacg gttacagccc agtttccagg ggcgtgtggg       120
cttcgctaca ggaatccagt gtctcagtgt atgagaggtg tccggctggt agaaggaatt       180
ctgcatgccc cagatgctgg ctggggaaat ctggtgtatg ttgtcaacta tccaaaagat       240
aacaaaagaa aaatggatga gacagatgct tcatcagcag tgaaagtgaa aagagcagtc       300
cagaaaacat ccgatttaat agtgttgggt ctcccatgga aaacaaccga acaggacctg       360
aaagagtatt ttagtacctt tggagaagtt cttatggtgc aggtcaagaa agatcttaag       420
actggtcatt caaagggtt tggctttgtt cgttttacgg aatatgaaac acaagtgaaa       480
gtaatgtcac agcgacatat gatagatgga cgatggtgtg actgcaaact tcctaattct       540
aagcaaagcc aagatgagcc tttgagaagc agaaaagtgt tgtggggcg ctgtacagag       600 gacatgactg aggatgagct gcgggagttc ttctctcagt acggggatgt gatggatgtc       660
ttcatcccca agccattcag ggcctttgcc tttgttacat ttgcagatga tcagattgcg       720
cagtctcttt gtggagagga cttgatcatt aaaggaatca gcgttcatat atccaatgcc       780
gaacctaagc acaatagcaa tagacagtta gaaagaagtg gaagatttgg tggtaatcca       840
ggtggctttg ggaatcaggg tggatttggt aatagcagag ggtgggagc tggtttggga       900 aacaatcaag gtagtaatat gggtggtggg atgaactttg gtgcgttcag cattaatcca       960
```

```
gccatgatgg ctgccgccca ggcagcacta cagagcagtt ggggtatgat gggcatgtta    1020
gccagccagc agaaccagtc aggcccatcg ggtaataacc aaaaccaagg caacatgcag    1080
agggagccaa accaggcctt cggttctgga ataactctt atagtggctc taattctggt     1140
gcagcaattg gttggggatc agcatccaat gcagggtcgg gcagtggttt taatggaggc    1200
tttggctcaa gcatggattc taagtcttct ggctggggaa tg                       1242

<210> SEQ ID NO 2
<211> LENGTH: 522
<212> TYPE: DNA
<213> ORGANISM: Artificial Sequence
<220> FEATURE:
<223> OTHER INFORMATION: VC173

<400> SEQUENCE: 2
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagct gatctgcacc accggcaagc tgcccgtgcc ctggcccacc    180
ctcgtgacca ccctgggcta cggcctgcag tgcttcgccc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca ccgccgacaa gcagaagaac    480
ggcatcaagg ccaacttcaa gatccgccac aacatcgagt ag                       522

<210> SEQ ID NO 3
<211> LENGTH: 249
<212> TYPE: DNA
<213> ORGANISM: Artificial Sequence
<220> FEATURE:
<223> OTHER INFORMATION: VC155

<400> SEQUENCE: 3
cagaagaacg gcatcaaggc caacttcaag atccgccaca acatcgagga cggcggcgtg     60
cagctcgccg accactacca gcagaacacc cccatcggcg acggccccgt gctgctgccc    120
gacaaccact acctgagcta ccagtccaaa ctgagcaaag accccaacga gaagcgcgat    180
cacatggtcc tgctggagtt cgtgaccgcc gccgggatca ctctcggcat ggacgagctg    240
tacaagtaa                                                            249

<210> SEQ ID NO 4
<211> LENGTH: 42
<212> TYPE: DNA
<213> ORGANISM: Artificial Sequence
<220> FEATURE:
<223> OTHER INFORMATION: VC173 linker

<400> SEQUENCE: 4
acgcgtacgc ggccgctcga gtctagaaga tccatcgcca cc                        42

<210> SEQ ID NO 5
<211> LENGTH: 24
<212> TYPE: DNA
<213> ORGANISM: Artificial Sequence
<220> FEATURE:
<223> OTHER INFORMATION: VC155 linker

<400> SEQUENCE: 5
```

```
acgcgtacgc ggccgctcga gaag                                          24
```

<210> SEQ ID NO 6
<211> LENGTH: 1806
<212> TYPE: DNA
<213> ORGANISM: Artificial Sequence
<220> FEATURE:
<223> OTHER INFORMATION: TDP43-VC173 linker-VC173

<400> SEQUENCE: 6

```
atgtctgaat atattcgggt aaccgaagat gagaacgatg agcccattga ataccatcg     60
gaagacgatg ggacggtgct gctctccacg gttacagccc agtttccagg ggcgtgtggg   120
cttcgctaca ggaatccagt gtctcagtgt atgagaggtg tccggctggt agaaggaatt   180
ctgcatgccc cagatgctgg ctggggaaat ctggtgtatg ttgtcaacta tccaaaagat   240
aacaaaagaa aaatggatga gacagatgct tcatcagcag tgaaagtgaa agagcagtc    300
cagaaaacat ccgatttaat agtgttgggt ctcccatgga aaacaaccga acaggacctg   360
aaagagtatt ttagtaccct tggagaagtt cttatggtgc aggtcaagaa agatcttaag   420
actggtcatt caaaggggtt tggctttgtt cgttttacgg aatatgaaac acaagtgaaa   480
gtaatgtcac agcgacatat gatagatgga cgatggtgtg actgcaaact tcctaattct   540
aagcaaagcc aagatgagcc tttgagaagc agaaaagtgt ttgtggggcg ctgtacagag   600
gacatgactg aggatgagct gcgggagttc ttctctcagt acggggatgt gatggatgtc   660
ttcatcccca agccattcag ggcctttgcc tttgttacat ttgcagatga tcagattgcg   720
cagtctcttt gtggagagga cttgatcatt aaaggaatca gcgttcatat atccaatgcc   780
gaacctaagc acaatagcaa tagacagtta gaaagaagtg gaagattggg tggtaatcca   840
ggtggctttg gaatcaggg tggatttggt aatagcagag gggtggagc tggtttggga    900
aacaatcaag gtagtaatat gggtggtggg atgaactttg gtgcgttcag cattaatcca   960
gccatgatgg ctgccgccca gcagcactt cagagcagtt ggggtatgat gggcatgtta   1020
gccagccagc agaaccagtc aggcccatcg ggtaataacc aaaaccaagg caacatgcag  1080
agggagccaa accaggcctt cggttctgga ataactctt atagtggctc taattctggt   1140
gcagcaattg ttggggatc agcatccaat gcagggtcgg gcagtggttt taatggaggc  1200
tttggctcaa gcatggattc taagtcttct ggctggggaa tgacgcgtac gcggccgctc 1260
gagtctagaa gatccatcgc caccatggtg agcaagggcg aggagctgtt caccggggtg 1320
gtgcccatcc tggtcgagct ggacggcgac gtaaacggcc acaagttcag cgtgtccggc 1380
gagggcgagg gcgatgccac ctacggcaag ctgaccctga agctgatctg caccaccggc 1440
aagctgcccg tgccctggcc caccctcgtg accaccctgg ctacggcct gcagtgcttc  1500
gcccgctacc ccgaccacat gaagcagcac gacttcttca gtccgccat gcccgaaggc  1560
tacgtccagg agcgcaccat cttcttcaag gacgacggca actacaagac ccgcgccgag 1620
gtgaagttcg agggcgacac cctggtgaac cgcatcgagc tgaagggcat cgacttcaag 1680
gaggacggca acatcctggg gcacaagctg gagtacaact acaacagcca caacgtctat 1740
atcaccgccg acaagcagaa gaacggcatc aaggccaact tcaagatccg ccacaacatc 1800
gagtag                                                            1806
```

<210> SEQ ID NO 7
<211> LENGTH: 1515
<212> TYPE: DNA

<213> ORGANISM: Artificial Sequence
<220> FEATURE:
<223> OTHER INFORMATION: TDP43-VC155 linker-VC155

<400> SEQUENCE: 7

```
atgtctgaat atattcgggt aaccgaagat gagaacgatg agcccattga ataccatcg      60
gaagacgatg ggacggtgct gctctccacg gttacagccc agtttccagg ggcgtgtggg   120
cttcgctaca ggaatccagt gtctcagtgt atgagaggtg tccggctggt agaaggaatt   180
ctgcatgccc cagatgctgg ctggggaaat ctggtgtatg ttgtcaacta tccaaaagat   240
aacaaaagaa aaatggatga cagatgct tcatcagcag tgaaagtgaa aagagcagtc     300
cagaaaacat ccgatttaat agtgttgggt ctcccatgga aacaaccga acaggacctg    360
aaagagtatt ttagtacctt tggagaagtt cttatggtgc aggtcaagaa agatcttaag   420
actggtcatt caaaggggtt tggctttgtt cgttttacgg aatatgaaac acaagtgaaa   480
gtaatgtcac agcgacatat gatagatgga cgatggtgtg actgcaaact tcctaattct   540
aagcaaagcc aagatgagcc tttgagaagc agaaaagtgt tgtggggcg ctgtacagag    600
gacatgactg aggatgagct gcgggagttc ttctctcagt acggggatgt gatggatgtc   660
ttcatcccca agccattcag ggcctttgcc tttgttacat ttgcagatga tcagattgcg   720
cagtctcttt gtggagagga cttgatcatt aaaggaatca gcgttcatat atccaatgcc   780
gaacctaagc acaatagcaa tagacagtta gaaagaagtg gaagatttgg tggtaatcca   840
ggtggctttg ggaatcaggg tggatttggt aatagcagag ggggtggagc tggtttggga   900
aacaatcaag gtagtaatat gggtggtggg atgaactttg gtgcgttcag cattaatcca   960
gccatgatgg ctgccgccca ggcagcacta cagagcagtt ggggtatgat gggcatgtta  1020
gccagccagc agaaccagtc aggcccatcg ggtaataacc aaaaccaagg caacatgcag  1080
agggagccaa accaggcctt cggttctgga ataactctt atagtggctc taattctggt   1140
gcagcaattg gttggggatc agcatccaat gcagggtcgg gcagtggttt taatggaggc  1200
tttggctcaa gcatggattc taagtcttct ggctggggaa tgacgcgtac gcggccgctc  1260
gagaagcaga gaacggcat caaggccaac ttcaagatcc gccacaacat cgaggacggc   1320
ggcgtgcagc tcgccgacca ctaccagcag aacaccccca tcggcgacgg ccccgtgctg  1380
ctgcccgaca ccactacct gagctaccag tccaaactga gcaaagaccc caacgagaag  1440
cgcgatcaca tggtcctgct ggagttcgtg accgccgccg ggatcactct cggcatggac  1500
gagctgtaca agtaa                                                    1515
```